US012588799B2

(12) United States Patent
Usuda

(10) Patent No.: US 12,588,799 B2
(45) Date of Patent: Mar. 31, 2026

(54) IMAGE DIAGNOSIS ASSISTANCE APPARATUS, ENDOSCOPE SYSTEM, IMAGE DIAGNOSIS ASSISTANCE METHOD, AND IMAGE DIAGNOSIS ASSISTANCE PROGRAM

(71) Applicant: FUJIFILM Corporation, Tokyo (JP)

(72) Inventor: Toshihiro Usuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 719 days.

(21) Appl. No.: 17/591,343

(22) Filed: Feb. 2, 2022

(65) Prior Publication Data

US 2022/0151462 A1    May 19, 2022

Related U.S. Application Data

(63) Continuation of application No. PCT/JP2020/029967, filed on Aug. 5, 2020.

(30) Foreign Application Priority Data

Aug. 13, 2019    (JP) ................................ 2019-148334

(51) Int. Cl.
*A61B 1/00* (2006.01)
*A61B 1/045* (2006.01)
(52) U.S. Cl.
CPC ...... *A61B 1/00043* (2013.01); *A61B 1/00013* (2013.01); *A61B 1/045* (2013.01)
(58) Field of Classification Search
CPC .. A61B 1/00043; A61B 1/00013; A61B 1/045
(Continued)

(56) References Cited

U.S. PATENT DOCUMENTS 7,479,990 B2 * 1/2009 Imaizumi ............... A61B 1/043
                                                             348/370
8,681,208 B2 * 3/2014 Yoshino ............... A61B 1/0646
                                                              348/75
(Continued)

FOREIGN PATENT DOCUMENTS

JP        2006-129950 A     5/2006
JP        2015-112429 A     6/2015
(Continued)

OTHER PUBLICATIONS

JP2015112429 English Translation (Year: 2015).*
(Continued)

*Primary Examiner* — Michael J Carey
*Assistant Examiner* — Megan Elizabeth Monahan
(74) *Attorney, Agent, or Firm* — Studebaker Brackett PLLC

(57)    ABSTRACT

An object of the present invention is to provide an image diagnosis assistance apparatus, an endoscope system, and an image diagnosis assistance method that are capable of appropriately performing reporting by using screen display and audio. An image diagnosis assistance apparatus according to a first aspect of the present invention includes an image acquiring unit that acquires a chronological medical image, a recognizing unit that performs recognition of a region of interest in the acquired medical image, a reporting unit that performs reporting of a result of the recognition by using screen display and audio, and a determining unit that makes a determination on an examination status. The reporting unit performs reporting by using the screen display regardless of a result of the determination, and performs reporting by using the audio in either of a first mode of using audio having a first reporting level and a second mode of using audio having a second reporting level lower than the (Continued)

first reporting level, in accordance with a result of the determination.

12 Claims, 11 Drawing Sheets

(58) Field of Classification Search
USPC ........................................................ 362/574
See application file for complete search history.

(56) References Cited

U.S. PATENT DOCUMENTS

| | | | | | |
|---|---|---|---|---|---|
| 2006/0280347 | A1* | 12/2006 | Shirahata | ............... | A61B 6/463 |
| | | | | | 382/128 |
| 2007/0153542 | A1* | 7/2007 | Gono | .................... | A61B 1/063 |
| | | | | | 362/574 |
| 2009/0118578 | A1* | 5/2009 | Takasugi | .............. | A61B 5/0084 |
| | | | | | 600/109 |
| 2016/0283681 | A1 | 9/2016 | Falck et al. | | |

| | | | | | |
|---|---|---|---|---|---|
| 2020/0008653 | A1 | 1/2020 | Kamon | | |
| 2020/0242766 | A1 | 7/2020 | Endo | | |
| 2021/0022586 | A1* | 1/2021 | Mori | ...................... | A61B 1/045 |

FOREIGN PATENT DOCUMENTS

| | | | | | |
|---|---|---|---|---|---|
| JP | 2015112429 | * | 6/2015 | .............. | A61B 1/00 |
| JP | 2016-540552 | A | 12/2016 | | |
| WO | 2005/011501 | A1 | 2/2005 | | |
| WO | 2018/179991 | A1 | 10/2018 | | |
| WO | 2019/078102 | A1 | 4/2019 | | |

OTHER PUBLICATIONS

An Office Action; "Notice of Reasons for Refusal," mailed by the Japanese Patent Office on Dec. 23, 2022, which corresponds to Japanese Patent Application No. 2021-539230 and is related to U.S. Appl. No. 17/591,343; with English language translation.
International Search Report issued in PCT/JP2020/029967; mailed Sep. 29, 2020.
International Preliminary Report on Patentability and Written Opinion issued in PCT/JP2020/029967; issued Feb. 8, 2022.

* cited by examiner

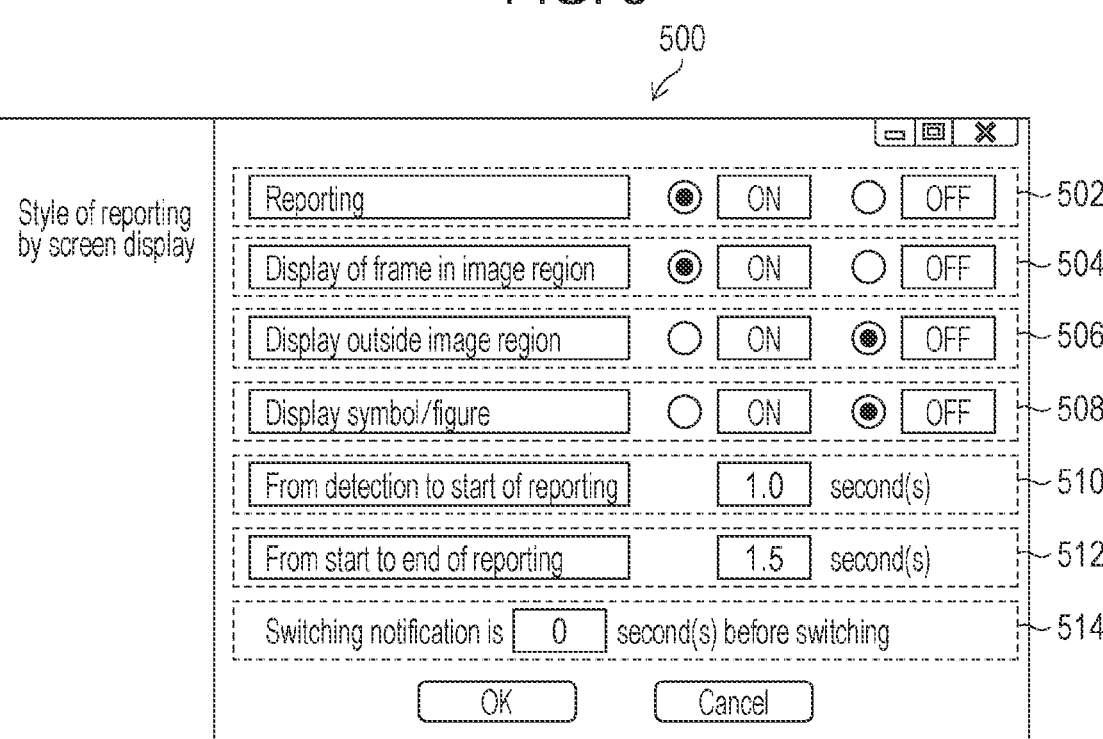

| Style of reporting by screen display | | | | | |
|---|---|---|---|---|---|
| Reporting | ⦿ | ON | ◯ | OFF | ~502 |
| Display of frame in image region | ⦿ | ON | ◯ | OFF | ~504 |
| Display outside image region | ◯ | ON | ⦿ | OFF | ~506 |
| Display symbol/figure | ◯ | ON | ⦿ | OFF | ~508 |
| From detection to start of reporting | | 1.0 | second(s) | | ~510 |
| From start to end of reporting | | 1.5 | second(s) | | ~512 |
| Switching notification is | 0 | second(s) before switching | | | ~514 |

OK          Cancel

| Style of reporting by audio | | | | | |
|---|---|---|---|---|---|
| Reporting by audio | ⦿ | ON | ◯ | OFF | ~522 |
| 《Criteria for mode switching》 | | | | | |
| Feature of region of interest | ⦿ | ON | ◯ | OFF | ~524 |
| Duration of first mode | ◯ | ON | ⦿ | OFF | ~526 |
| Examination status | ◯ | ON | ⦿ | OFF | ~528 |

OK          Cancel

530

Mode switching based on feature of region of interest

| Size of region of interest | ◉ | 20 | mm² | ~532 |
| Shape of region of interest | ○ | Circular ▼ | | ~534 |
| Position of region of interest | ○ | Center ▼ | | ~536 |
| Number of regions of interest | ○ | 3 | or more | ~538 |
| Lesion type 1 | ◉ | Benign ▼ | | ~540 |
| Lesion type 2 | ○ | None ▼ | | ~542 |

OK          Cancel

550

Mode switching based on duration of first mode

| Duration of first mode | 2.0 | second(s) | ~552 |

OK          Cancel 602     604

602     600

606

608

607

602

600     601

605

603

602

600

604

602

610

614A      612A

600

604

602

610

614B      612B

IMAGE DIAGNOSIS ASSISTANCE APPARATUS, ENDOSCOPE SYSTEM, IMAGE DIAGNOSIS ASSISTANCE METHOD, AND IMAGE DIAGNOSIS ASSISTANCE PROGRAM

CROSS-REFERENCE TO RELATED APPLICATIONS

The present application is a Continuation of PCT International Application No. PCT/JP2020/029967 filed on Aug. 5, 2020 claiming priority under 35 U.S.C § 119(a) to Japanese Patent Application No. 2019-148334 filed on Aug. 13, 2019. Each of the above applications is hereby expressly incorporated by reference, in its entirety, into the present application.

BACKGROUND OF THE INVENTION

1. Field of the Invention

The present invention relates to an image diagnosis assistance apparatus, an endoscope system, an image diagnosis assistance method, and an image diagnosis assistance program that report a recognition result of a medical image.

2. Description of the Related Art

To prevent a region of interest, such as a lesion, from being overlooked by an endoscope operator, reporting techniques of displaying a detected region of interest in an emphasized manner and outputting an alert sound are developed. For example, JP2006-129950A describes a capsule endoscope that outputs a notification sound (pre-warning sound, report sound, termination sound) providing a notification indicating that a feature image is to be displayed.

SUMMARY OF THE INVENTION

For several seconds immediately after a region of interest comes into sight, a viewpoint frequently changes and the risk of oversight is high, and thus necessity for reporting is high. On the other hand, the timing at which reporting is necessary is about several seconds from when a region of interest is detected. Once an operator has found a region of interest and started detailed observation, reporting may disturb the observation, reduce the operator's motivation to perform an operation, or cause a delay in finding another region of interest. In particular, reporting by audio has a high reporting level but may drown audio of another device, such as a heartrate meter, and thus special measures are required.

However, the existing technique as described in JP2006-129950A mentioned above does not sufficiently take these points into consideration.

The present invention has been made in view of these circumstances, and it is an object of the present invention to provide an image diagnosis assistance apparatus, an endoscope system, an image diagnosis assistance method, and an image diagnosis assistance program that are capable of appropriately performing reporting by using screen display and audio.

To achieve the above-described object, an image diagnosis assistance apparatus according to a first aspect of the present invention includes an image acquiring unit that acquires a chronological medical image, a recognizing unit that performs recognition of a region of interest in the acquired medical image, a reporting unit that performs reporting of a result of the recognition by using screen display and audio, and a determining unit that makes a determination on an examination status. The reporting unit performs reporting by using the screen display regardless of a result of the determination, and performs reporting by using the audio in either of a first mode of using audio having a first reporting level and a second mode of using audio having a second reporting level lower than the first reporting level, in accordance with a result of the determination.

In the first aspect, the reporting unit performs reporting by using the screen display regardless of a result of the determination, and performs reporting by using the audio in either of the first mode of using audio having the first reporting level and the second mode of using audio having the second reporting level lower than the first reporting level, in accordance with a result of the determination. Accordingly, audio having an appropriate reporting level can be used in accordance with an examination status, and reporting by the screen display and the audio can be appropriately performed.

In the first aspect, the "region of interest" may include a legion region, a candidate lesion region, or a region that has been treated, and the "recognition" of the region of interest may include determination (detection, measurement, classification, or the like) of the presence, number, position, size, shape, type, or motion in an image of the region of interest, the level of lesion, or the like. The "acquisition of a medical image" includes sequentially acquiring a plurality of medicate images captured at a determined frame rate. The acquisition may or may not be performed in real time. The image acquiring unit may acquire a plurality of medical images by capturing images using an imaging apparatus including an imaging optical system and an imaging element, or may acquire a plurality of medical images recorded in advance via a network and/or a recording medium.

The image diagnosis assistance apparatus according to the first aspect can be implemented as, for example, a processor of a medical image processing system, but is not limited to such an aspect. The "medical image" is an image acquired as a result of imaging, measurement, or the like performed on a living body, such as a human body, for the purpose of diagnosis, treatment, measurement, or the like, and may be, for example, an endoscopic image, an ultrasound image, a computed tomography (CT) image, or a magnetic resonance imaging (MRI) image.

In an image diagnosis assistance apparatus according to a second aspect, in the first aspect, the determining unit determines a time during which reporting in the first mode is continuously being performed on the same region of interest, and in a case where the time is longer than or equal to a threshold value, the reporting unit is switched to the second mode and performs reporting. In a case where the duration of reporting in the first mode for the same region of interest is longer than or equal to the threshold value, the reporting may disturb observation, reduce operator's motivation to perform an operation, or cause a delay in finding another region of interest. Thus, the reporting unit is switched to the second mode having a lower reporting level than the first mode and performs reporting. In the second aspect, suspension of reporting in the first mode for a short time (shorter than a determined time) may be regarded as "reporting is continued".

In an image diagnosis assistance apparatus according to a third aspect, in the first or second aspect, the reporting unit performs reporting in the second mode in a case where a result of the determination indicates any one or more of that the medical image is being displayed in an enlarged view, that observation with pigment is being performed, that observation with special light is being performed, that treatment is being performed, and that washing is being performed. In the third aspect, in a case where the medical image is being displayed in an enlarged view, for example, it is considered that a user has been aware of a region of interest, and reporting is performed in the second mode having a lower reporting level.

In an image diagnosis assistance apparatus according to a fourth aspect, in any one of the first to third aspects, the recognizing unit recognizes a feature of the region of interest, the determining unit determines whether the feature satisfies a criterion, and the reporting unit performs reporting in the second mode in a case where a determination is made that the feature satisfies the criterion. In the fourth aspect, there may be one or more "features" and one or more "criteria". A "feature" and a "criterion" may be set in accordance with a user setting.

In an image diagnosis assistance apparatus according to a fifth aspect, in the fourth aspect, the recognizing unit recognizes, as the feature, at least one of a size, a position, a shape, a number, or a lesion type of the region of interest, and the reporting unit performs reporting in the second mode in a case where the recognized feature satisfies the criterion. The fifth aspect specifically defines the "feature" of a region of interest, and the "criterion" for the feature may be set for each of a size, a position, a shape, a number, and a lesion type. The criterion may be, for example, the size is larger than or equal to a determined area, the position is a specific position (for example, near the center) of a medical image, the shape of the region of interest is a specific shape, the number of regions of interest is larger than or equal to a determined number, the region of interest is of a specific lesion type, or the like. In the fifth aspect, when "the size of the region of interest is larger than or equal to a determined area" or the like, it is considered that the user has been aware of the region of interest, and reporting is performed in the second mode having a lower reporting level.

In an image diagnosis assistance apparatus according to a sixth aspect, in any one of the first to fifth aspects, the reporting unit performs the reporting in the second mode by at least one of making volume of the audio lower than in the first mode, making a tone of the audio lower than in the first mode (lowering sound), making pitch of the audio lower than in the first mode, or stopping reporting by the audio. The sixth aspect defines a specific method for lowering the reporting level.

To achieve the above-described object, an endoscope system according to a seventh aspect of the present invention includes the image diagnosis assistance apparatus according to any one of the first to sixth aspects, a display apparatus that displays the medical image, and an endoscope that is to be inserted into a subject and that has an imaging unit that captures the medical image. The endoscope system according to the seventh aspect includes the image diagnosis assistance apparatus according to any one of the first to sixth aspects, and is thus capable of appropriately performing reporting by using screen display and audio.

To achieve the above-described object, an image diagnosis assistance method according to an eighth aspect of the present invention includes an image acquisition step of acquiring a chronological medical image, a recognition step of performing recognition of a region of interest in the acquired medical image, a reporting step of performing reporting of a result of the recognition by using screen display and audio, and a determination step of making a determination on an examination status. The reporting step performs reporting by using the screen display regardless of a result of the determination, and performs reporting by using the audio in either of a first mode of using audio having a first reporting level and a second mode of using audio having a second reporting level lower than the first reporting level, in accordance with a result of the determination. According to the eighth aspect, as in the first aspect, it is possible to appropriately perform reporting by using screen display and audio.

The image diagnosis assistance method according to the eighth aspect may further include configurations similar to those according to the second to sixth aspects.

To achieve the above-described object, an image diagnosis assistance program according to a ninth aspect of the present invention is an image diagnosis assistance program that causes a computer to execute an image acquisition function of acquiring a chronological medical image, a recognition function of performing recognition of a region of interest in the acquired medical image, a reporting function of performing reporting of a result of the recognition by using screen display and audio, and a determination function of making a determination on an examination status. The reporting function performs reporting by using the screen display regardless of a result of the determination, and performs reporting by using the audio in either of a first mode of using audio having a first reporting level and a second mode of using audio having a second reporting level lower than the first reporting level, in accordance with a result of the determination. According to the ninth aspect, as in the first and eighth aspects, it is possible to appropriately perform reporting by using screen display and audio. The image diagnosis assistance program according to the ninth aspect may further include configurations (functions) similar to those according to the second to sixth aspects. In addition, a non-transitory recording medium storing computer-readable code of the image diagnosis assistance program of these aspects is also included in an aspect of the present invention.

As described above, the image diagnosis assistance apparatus, the endoscope system, the image diagnosis assistance method, and the image diagnosis assistance program according to the present invention are capable of appropriately performing reporting by using screen display and audio.

BRIEF DESCRIPTION OF THE DRAWINGS

FIG. 8 is a diagram illustrating an example of a setting screen for a style of reporting by screen display;

FIG. 9 is a diagram illustrating an example of a setting screen for a style of reporting by audio;

DESCRIPTION OF THE PREFERRED EMBODIMENTS

Hereinafter, an embodiment of an image diagnosis assistance apparatus, an endoscope system, an image diagnosis assistance method, and an image diagnosis assistance program according to the present invention will be described in detail with reference to the accompanying drawings.

First Embodiment

Configuration of Endoscope System

Figure 1:
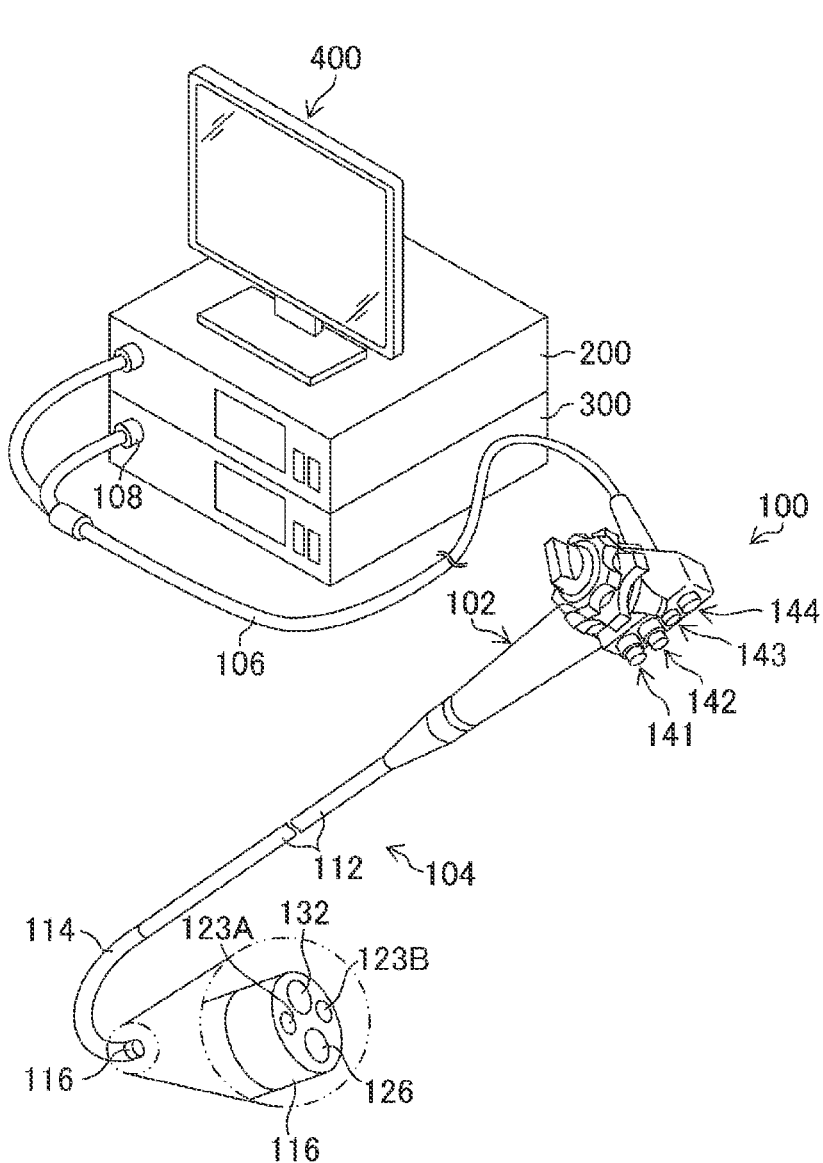
FIG. 1 is a diagram illustrating the configuration of an endoscope system according to a first embodiment.
Figure 2:
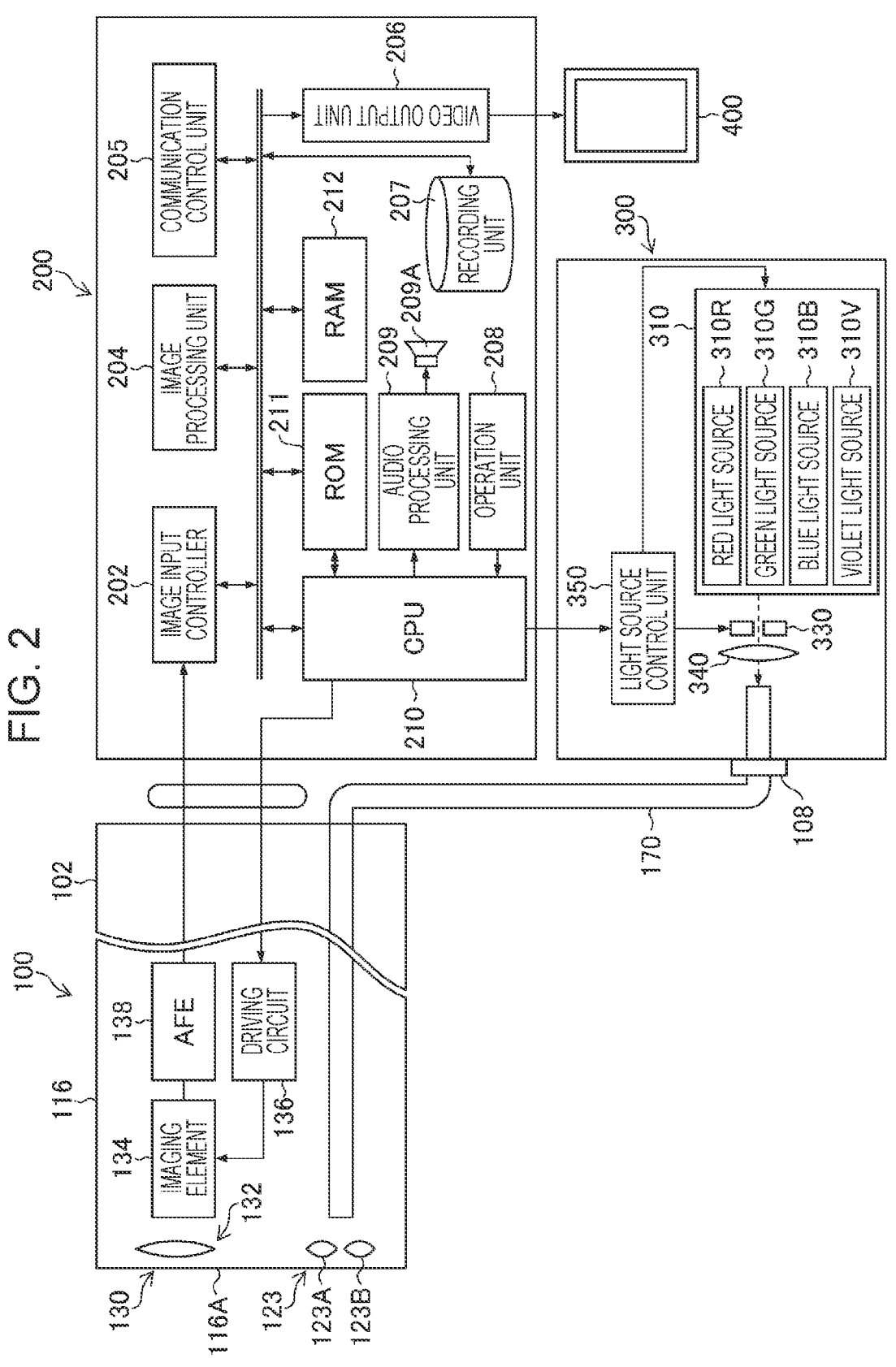
FIG. 2 is another diagram illustrating the configuration of the endoscope system.

FIG. 1 is an external appearance diagram of an endoscope system 10 (an image diagnosis assistance apparatus, a medical image processing apparatus, an endoscope system), and FIG. 2 is a block diagram illustrating the configuration of a main part of the endoscope system 10. As illustrated in FIGS. 1 and 2, the endoscope system 10 is constituted by an endoscope 100 (a medical apparatus, an endoscope, an endoscope main body), a processor 200 (an image diagnosis assistance apparatus, a medical image processing apparatus), a light source apparatus 300 (a light source apparatus), and a monitor 400 (a display apparatus).

Configuration of Endoscope

The endoscope 100 includes a handheld operation section 102 and an insertion section 104 that communicates with the handheld operation section 102. An operator (a user) operates the handheld operation section 102 while grasping it and inserts the insertion section 104 into a body of a subject (a living body) to perform observation. The handheld operation section 102 is provided with an air/water supply button 141, a suction button 142, a function button 143 to which various functions are allocated, and an imaging button 144 for receiving an imaging instruction operation (a still image, a moving image). The insertion section 104 is constituted by a soft part 112, a bending part 114, and a tip rigid part 116, which are arranged in this order from the handheld operation section 102 side. That is, the bending part 114 is connected to a base end side of the tip rigid part 116, and the soft part 112 is connected to a base end side of the bending part 114. The handheld operation section 102 is connected to a base end side of the insertion section 104. The user is able to change the orientation of the tip rigid part 116 in an up, down, left, or right direction by causing the bending part 114 to bend by operating the handheld operation section 102. The tip rigid part 116 is provided with an imaging optical system 130, an illumination unit 123, a forceps port 126, and so forth (see FIGS. 1 and 2).

During observation or treatment, an operation of an operation unit 208 (see FIG. 2) enables white light and/or narrow-band light (one or more of red narrow-band light, green narrow-band light, blue narrow-band light, and violet narrow-band light) to be radiated from illumination lenses 123A and 123B of the illumination unit 123. In addition, an operation of the air/water supply button 141 enables washing water to be ejected from a water supply nozzle that is not illustrated, so that an imaging lens 132 (an imaging lens, an imaging unit) of the imaging optical system 130 and the illumination lenses 123A and 123B can be washed. The forceps port 126 opening in the tip rigid part 116 communicates with a pipe line that is not illustrated, so that a treatment tool that is not illustrated and is for extirpating a tumor or the like can be inserted into the pipe line and necessary treatment can be given to a subject by moving the treatment tool forward or backward as appropriate.

As illustrated in FIGS. 1 and 2, the imaging lens 132 (an imaging unit) is disposed on a distal-end-side surface 116A of the tip rigid part 116. A complementary metal-oxide semiconductor (CMOS) imaging element 134 (an imaging element, an imaging unit), a driving circuit 136, and an analog front end (AFE) 138 (an imaging unit) are disposed behind the imaging lens 132, and these elements output an image signal. The imaging element 134 is a color imaging element and includes a plurality of pixels constituted by a plurality of light-receiving elements arranged in a matrix (arranged two-dimensionally) in a specific pattern arrangement (Bayer arrangement, X-Trans (registered trademark) arrangement, honeycomb arrangement, or the like). Each pixel of the imaging element 134 includes a microlens, a red (R), green (G), or blue (B) color filter, and a photoelectric conversion unit (a photodiode or the like). The imaging optical system 130 is capable of generating a color image from pixel signals of three colors, red, green, and blue, and is also capable of generating an image from pixel signals of any one or two colors among red, green, and blue. In the first embodiment, a description will be given of a case where the imaging element 134 is a CMOS imaging element, but the imaging element 134 may be a charge coupled device (CCD) imaging element. Each pixel of the imaging element 134 may further include a violet color filter corresponding to a violet light source 310V and/or an infrared filter corresponding to an infrared light source.

An optical image of a subject is formed on a light-receiving surface (an imaging surface) of the imaging element 134 by the imaging lens 132, converted into an electric signal, output to the processor 200 through a signal cable that is not illustrated, and converted into a video signal. Accordingly, an endoscopic image is displayed on the monitor 400, which is connected to the processor 200.

The illumination lenses 123A and 123B of the illumination unit 123 are provided next to the imaging lens 132 on the distal-end-side surface 116A of the tip rigid part 116. An emission end of a light guide 170, which will be described below, is disposed behind the illumination lenses 123A and 123B. The light guide 170 extends through the insertion section 104, the handheld operation section 102, and a universal cable 106, and an incidence end of the light guide 170 is located in a light guide connector 108.

A user performs imaging (under control of the imaging unit and an image acquiring unit 220) at a determined frame rate while inserting or removing the endoscope 100 (the insertion section 104) having the above-described configuration into or from a living body as a subject, thereby being capable of sequentially capturing images of the inside of the living body.

Configuration of Light Source Apparatus

As illustrated in FIG. 2, the light source apparatus 300 is constituted by a light source 310 for illumination, a diaphragm 330, a condenser lens 340, a light source control unit 350, and so forth, and causes observation light to enter the light guide 170. The light source 310 includes a red light source 310R, a green light source 310G, a blue light source 310B, and the violet light source 310V that radiate red narrow-band light, green narrow-band light, blue narrow-band light, and violet narrow-band light, respectively, and is capable of radiating red narrow-band light, green narrow-band light, blue narrow-band light, and violet narrow-band light. The illuminance of observation light from the light source 310 is controlled by the light source control unit 350, which is capable of changing (increasing or decreasing) the illuminance of observation light or stopping illumination as necessary.

The light source 310 is capable of emitting red narrow-band light, green narrow-band light, blue narrow-band light, and violet narrow-band light in any combination. For example, the light source 310 is capable of simultaneously emitting red narrow-band light, green narrow-band light, blue narrow-band light, and violet narrow-band light to radiate white light (normal light) as observation light, and is also capable of emitting any one or two of red narrow-band light, green narrow-band light, blue narrow-band light, and violet narrow-band light to radiate narrow-band light (special light). The light source 310 may further include an infrared light source that radiates infrared light (an example of narrow-band light). Alternatively, with use of a light source that radiates white light and a filter that allows white light and each narrow-band light to pass therethrough, white light or narrow-band light may be radiated as observation light.

Wavelength Range of Light Source

The light source 310 may be a light source that generates light in a white range or light in a plurality of wavelength ranges as the light in the white range, or may be a light source that generates light in a specific wavelength range narrower than the white wavelength range. The specific wavelength range may be a blue range or green range in a visible range, or may be a red range in the visible range. In a case where the specific wavelength range is the blue range or green range in the visible range, the specific wavelength range may include a wavelength range of 390 nm or more and 450 nm or less or a wavelength range of 530 nm or more and 550 nm or less, and the light in the specific wavelength range may have a peak wavelength in the wavelength range of 390 nm or more and 450 nm or less or the wavelength range of 530 nm or more and 550 nm or less. In a case where the specific wavelength range is the red range in the visible range, the specific wavelength range may include a wavelength range of 585 nm or more and 615 nm or less or a wavelength range of 610 nm or more and 730 nm or less, and the light in the specific wavelength range may have a peak wavelength in the wavelength range of 585 nm or more and 615 nm or less or the wavelength range of 610 nm or more and 730 nm or less.

The above-described wavelength range may include a wavelength range in which a light absorption coefficient is different between oxyhemoglobin and deoxyhemoglobin, and the light in the specific wavelength range may have a peak wavelength in the wavelength range in which the light absorption coefficient is different between oxyhemoglobin and deoxyhemoglobin. In this case, the specific wavelength range may include a wavelength range of 400±10 nm, a wavelength range of 440±10 nm, a wavelength range of 470±10 nm, or a wavelength range of 600 nm or more and 750 nm, and the light in the specific wavelength range may have a peak wavelength in the wavelength range of 400±10 nm, the wavelength range of 440±10 nm, the wavelength range of 470±10 nm, or the wavelength range of 600 nm or more and 750 nm or less.

The wavelength range of the light generated by the light source 310 may include a wavelength range of 790 nm or more and 820 nm or less or a wavelength range of 905 nm or more and 970 nm or less, and the light generated by the light source 310 may have a peak wavelength in the wavelength range of 790 nm or more and 820 nm or less or the wavelength range of 905 nm or more and 970 nm or less.

Alternatively, the light source 310 may include a light source that radiates excitation light whose peak is 390 nm or more and 470 nm or less. In this case, a medical image (an inside-of-living-body image) having information about fluorescence emitted by a fluorescent substance in a subject (a living body) can be acquired. In the case of acquiring a fluorescence image, a pigment for a fluorescence method (fluorescein, acridine orange, or the like) may be used.

It is preferable that the type of the light source 310 (a laser light source, a xenon light source, a light-emitting diode (LED) light source, or the like), the wavelength of the light source 310, the presence or absence of a filter for the light source 310, and so forth be determined in accordance with the type of photographic subject, an area of the photographic subject, the purpose of observation, or the like. It is also preferable that, during observation, the wavelengths of observation light be combined and/or switched in accordance with the type of photographic subject, an area of the photographic subject, the purpose of observation, or the like. In the case of switching the wavelength, for example, a disc-shaped filter (a rotary color filter) that is disposed in front of the light source and that is provided with a filter for transmitting or blocking light of a specific wavelength may be rotated to switch the wavelength of light to be radiated.

The imaging element used to carry out the present invention is not limited to a color imaging element in which color filters are disposed for the individual pixels, such as the imaging element 134, and may be a monochrome imaging element. In the case of using a monochrome imaging element, imaging can be performed in a frame sequential (color sequential) manner by sequentially switching the wavelength of observation light. For example, the wavelength of outgoing observation light may be sequentially switched among violet, blue, green, and red, or wide-band light (white light) may be radiated and the wavelength of outgoing observation light may be switched by using a rotary color filter (red, green, blue, violet, and the like). Alternatively, one or a plurality of types of narrow-band light (green, blue, violet, and the like) may be radiated and the wavelength of outgoing observation light may be switched by using a rotary color filter (green, blue, violet, and the like). The narrow-band light may be infrared light of two or more different wavelengths (first narrow-band light and second narrow-band light).

As a result of connecting the light guide connector 108 (see FIGS. 1 and 2) to the light source apparatus 300, observation light radiated by the light source apparatus 300 is transmitted through the light guide 170 to the illumination lenses 123A and 123B and is radiated from the illumination lenses 123A and 123B to an observation range.

Configuration of Processor

The configuration of the processor 200 will be described with reference to FIG. 2. In the processor 200, an image input controller 202 receives an image signal output from the endoscope 100, an image processing unit 204 performs necessary image processing thereon, and a video output unit 206 outputs a resulting image signal. Accordingly, an observation image (an inside-of-living-body image) is displayed on the monitor 400 (a display apparatus). These processing operations are performed under control by a central processing unit (CPU) 210. A communication control unit 205 controls communication, for a medical image or area information, with a hospital information system (HIS), a hospital local area network (LAN), and/or an external system or network that are not illustrated. In a recording unit 207 (a recording apparatus), an image of a subject (an endoscopic image, a medical image), information indicating a result of recognition (detection, classification, measurement, etc.), and the like are recorded (see FIG. 6 and the description related thereto). An audio processing unit 209 (a reporting unit) outputs a message (an audio signal) about recognition or reporting of a region of interest from a speaker 209A under control by the CPU 210 and the image processing unit 204.

A read only memory (ROM) 211 is a nonvolatile storage element (a non-transitory recording medium) and stores a computer-readable code of a program (including the image diagnosis assistance program according to the present invention) that causes the CPU 210 and/or the image processing unit 204 (a medical image processing apparatus, a computer) to execute various image processing methods. A random access memory (RAM) 212 is a storage element for temporary storage in various processing operations and can be used as a buffer at the time of acquiring an image.

A user is capable of providing an instruction to execute medical image processing or designating a condition necessary for the execution via the operation unit 208. A reporting unit 224, a determining unit 226, and a setting unit 228 are capable of causing the monitor 400 to display a screen of these instructions, a result of recognition, and so forth.

Functions of Image Processing Unit

Figure 3:
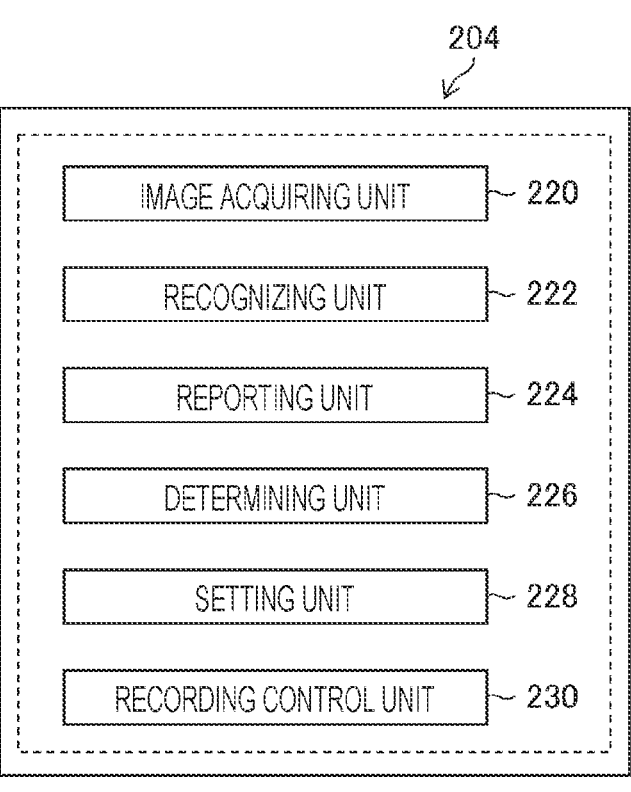
FIG. 3 is a functional block diagram of an image processing unit.

FIG. 3 is a functional block diagram of the image processing unit 204. The image processing unit 204 includes the image acquiring unit 220 (an image acquiring unit), a recognizing unit 222 (a recognizing unit), the reporting unit 224 (a reporting unit), the determining unit 226 (a determining unit), the setting unit 228 (a setting unit), and a recording control unit 230 (a recoding control unit). Medical image processing using these functions will be described in detail below.

The image processing unit 204 is capable of performing, with the above-described functions, calculation of a feature quantity of a medical image, processing of emphasizing or reducing a component of a specific frequency band, and processing of emphasizing or deemphasizing a specific target (a region of interest, blood vessels at a desired depth, or the like). The image processing unit 204 may include a special-light image acquiring unit that acquires a special-light image having information about a specific wavelength range on the basis of a normal-light image that is acquired by radiating light in the white range or light in a plurality of wavelength ranges as the light in the white range. In this case, a signal in the specific wavelength range can be acquired through computation based on color information of RGB (R: red, G: green, B: blue) or CMY (C: cyan, M: magenta, Y: yellow) included in the normal-light image. In addition, the image processing unit 204 may include a feature quantity image generating unit that generates a feature quantity image through computation based on at least one of a normal-light image that is acquired by radiating light in the white range or light in a plurality of wavelength ranges as the light in the white range or a special-light image that is acquired by radiating light in a specific wavelength range, and may acquire and display the feature quantity image as a medical image. The above-described processing is performed under control by the CPU 210.

Implementation of Functions by Various Processors

The above-described functions of the individual units of the image processing unit 204 can be implemented by using various types of processors and a recording medium. The various types of processors include, for example, a central processing unit (CPU) which is a general-purpose processor that executes software (program) to implement various functions. Also, the various types of processors include a graphics processing unit (GPU) which is a processor dedicated to image processing, and a programmable logic device (PLD) which is a processor whose circuit configuration is changeable after manufacturing, such as a field programmable gate array (FPGA). In the case of performing learning and recognition of images as in the present invention, the configuration using a GPU is effective. Furthermore, the various types of processors include a dedicated electric circuit which is a processor having a circuit configuration designed exclusively for executing specific processing, such as an application specific integrated circuit (ASIC).

The function of each unit may be implemented by one processor or may be implemented by a plurality of processors of the same type or different types (for example, a combination of a plurality of FPGAs, a combination of a CPU and an FPGA, or a combination of a CPU and a GPU). A plurality of functions may be implemented by one processor. A first example of implementing a plurality of functions by one processor is that a combination of one or more CPUs and software constitutes one processor and the one processor implements the plurality of functions, as represented by a computer. A second example is that a processor that implements the functions of an entire system by one integrated circuit (IC) chip is used, as represented by a system on chip (SoC). In this way, various functions are configured as a hardware structure by using one or more of the above-described various types of processors. Furthermore, the hardware structure of the various types of processors is, more specifically, electric circuitry formed by combining circuit elements such as semiconductor elements. The electric circuitry may be electric circuitry that implements the above-described functions by using logical disjunction, logical conjunction, logical negation, exclusive disjunction, and logical operation as a combination thereof.

When the above-described processor or electric circuitry executes the software (program), the code of the software to be executed that is readable by a computer (for example, the various types of processors or electric circuitry constituting the image processing unit 204, and/or a combination thereof) is stored in a non-transitory recording medium, such as the read only memory (ROM) 211, and the computer refers to the software. The software stored in the non-transitory recording medium includes a program for executing the image diagnosis assistance method according to the present invention (image diagnosis assistance program) and data to be used for the execution (data used to specify an image processing condition or a reporting style). The code may be recorded on a non-transitory recording medium, such as a magneto-optical recording device of various types or a semiconductor memory, instead of the ROM 211. In the processing using the software, the random access memory (RAM) 212 may be used as a transitory storage region, for example, and data stored in an electrically erasable and programmable read only memory (EEPROM) that is not illustrated can be referred to, for example. The recording unit 207 may be used as a "non-transitory recording medium".

11 12

Recognizing Unit Using Learned Model

The above-described recognizing unit 222 (a recognizing unit: a detector, a classifier, a measurer) can be constituted by using a learned model (a model learned by using an image set constituted by captured images of a living body), such as a convolutional neural network (CNN) or a support vector machine (SVM). Hereinafter, a description will be given of a layer configuration in a case where the recognizing unit 222 is constituted by a CNN. The description will be given mainly of a case where the recognizing unit 222 is a detector (for detecting a region of interest). However, a similar layer configuration can be adopted for classification (discrimination) or measurement.

Examples of Layer Configuration of CNN

Figures 4A, 4B:
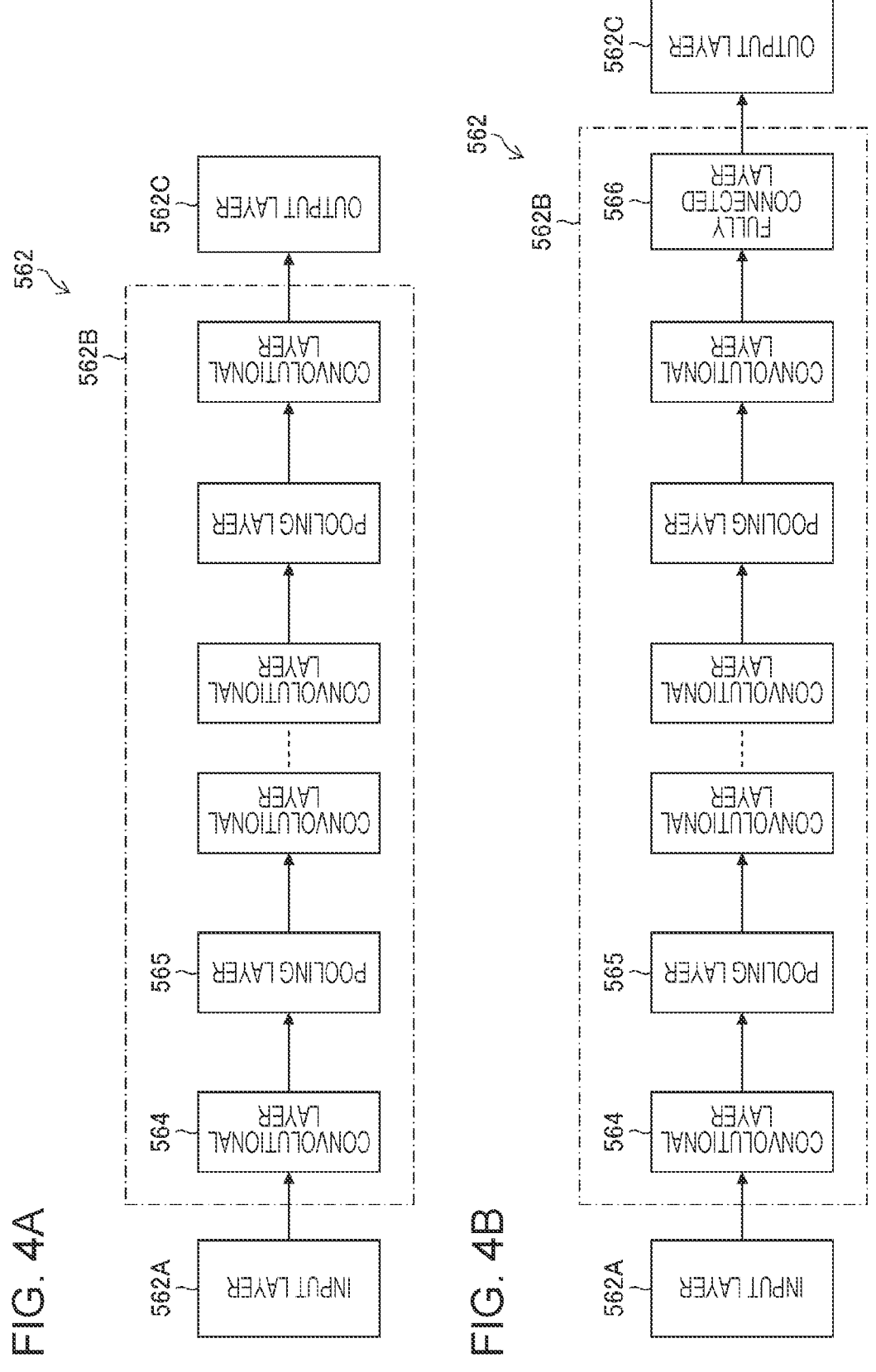
FIGS. 4A and 4B are diagrams illustrating configuration examples of a convolutional neural network.

FIGS. 4A and 4B are diagrams illustrating examples of the layer configuration of a CNN. In the example illustrated in FIG. 4A, a CNN 562 includes an input layer 562A, an intermediate layer 562B, and an output layer 562C. The input layer 562A receives an endoscopic image (medical image) acquired by the image acquiring unit 220 and outputs a feature quantity. The intermediate layer 562B includes convolutional layers 564 and pooling layers 565, and receives the feature quantity output from the input layer 562A and calculates another feature quantity. These layers each have a structure in which a plurality of "nodes" are connected by "edges" and hold a plurality of weight parameters. The values of the weight parameters change as learning progresses. The CNN 562 may include a fully connected layer 566 as in the example illustrated in FIG. 4B. The layer configuration of the CNN 562 is not limited to the configuration in which the convolutional layers 564 and the pooling layers 565 are alternately arranged, and may include a plurality of consecutive convolutional layers 564 or pooling layers 565 (for example, convolutional layers 564). Alternatively, a plurality of consecutive fully connected layers 566 may be included.

Processing in Intermediate Layer

The intermediate layer 562B calculates a feature quantity through convolutional operation and pooling processing. The convolutional operation performed in the convolutional layer 564 is processing of acquiring a feature map through convolutional operation using a filter, and plays a role in feature extraction such as edge extraction from an image. As a result of the convolutional operation using a filter, one-channel (one) "feature map" is created for one filter. The size of the "feature map" is scaled down by convolution and is reduced as convolution is performed in each layer. The pooling processing performed in the pooling layer 565 is processing of reducing (or enlarging) the feature map output through the convolutional operation to create a new feature map, and plays a role in giving robustness so that the extracted feature is not affected by parallel movement or the like. The intermediate layer 562B can be constituted by one or a plurality of layers that perform these processing operations.

Figure 5:
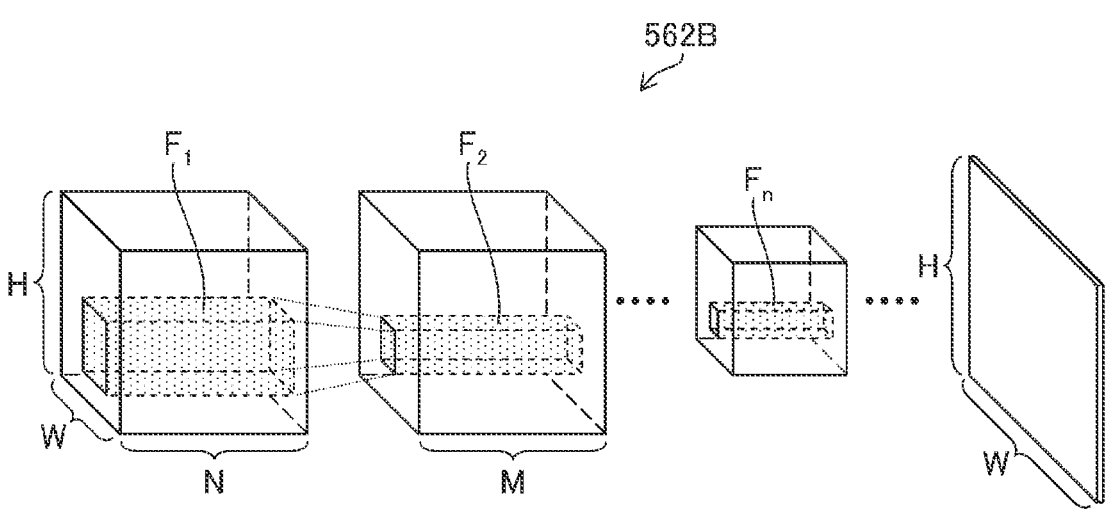
FIG. 5 is a diagram illustrating a state of convolutional processing using filters.

FIG. 5 is a schematic diagram illustrating an example configuration of the intermediate layer 562B of the CNN 562 illustrated in FIGS. 4A and 4B. In the first convolutional layer of the intermediate layer 562B, convolutional operation of an image set constituted by a plurality of medical images (a learning image set in the case of learning, and a recognition image set in the case of recognition) and a filter $F_1$ is performed. The image set is constituted by N (N-channel) images each having an image size in which the height is represented by H and the width is represented by W. In the case of inputting normal-light images, the images constituting an image set are three-channel images of red (R), green (G), and blue (B). The filter $F_1$ convoluted with this image set has a filter size of 5×5×N in the case of the filter having size 5 (5×5), for example, because the image set has N channels (N images). As a result of convolutional operation using the filter $F_1$, one-channel (one) "feature map" is created for one filter $F_1$. A filter $F_2$ used in the second convolutional layer has a filter size of 3×3×M in the case of the filter having size 3 (3×3), for example.

As in the first convolutional layer, in the second to n-th convolutional layers, convolutional operations using filters $F_2$ to $F_n$ are performed, respectively. The size of the "feature map" in the n-th convolutional layer is smaller than the size of the "feature map" in the second convolutional layer because scaling-down is performed in the convolutional layers or pooling layers in the preceding stages.

In the layers of the intermediate layer 562B, lower-order feature extraction (extraction of edges or the like) is performed in a convolutional layer near the input side, and higher-order feature extraction (extraction of features about the shape, structure, and the like of an object) is performed near the output side. In the case of performing segmentation for the purpose of measurement or the like, scaling-up is performed in a convolutional layer in a latter-half portion, and the "feature map" having the same size as the input image set can be obtained in the last convolutional layer. On the other hand, in the case of performing object detection, it is sufficient to output position information and thus scaling-up is not necessary.

The intermediate layer 562B may include a layer for performing batch normalization in addition to the convolutional layers 564 and the pooling layers 565. Batch normalization processing is the processing of normalizing a data distribution in units of mini batches for performing learning, and plays a role in quickly performing learning, reducing dependency on an initial value, suppressing overtraining, and so forth.

Processing in Output Layer

The output layer 562C is a layer that detects the position of a region of interest depicted in an input medical image (a normal-light image, a special-light image) on the basis of the feature quantity output from the intermediate layer 562B and outputs the result thereof. In the case of performing segmentation, the output layer 562C grasps the position of a region of interest depicted in an image in the pixel level by using the "feature map" acquired from the intermediate layer 562B. That is, the output layer 562C is capable of detecting, for each pixel of an endoscopic image, whether or not the pixel belongs to the region of interest, and outputting the detection result. On the other hand, in the case of performing object detection, determination in the pixel level is not necessary, and the output layer 562C outputs position information of a target.

The output layer 562C may execute discrimination (classification) of a lesion and output a discrimination result. For example, the output layer 562C may classify an endoscopic image into three categories "neoplastic", "non-neoplastic", and "others", and may output, as a discrimination result, three scores corresponding to "neoplastic", "non-neoplastic", and "others" (the sum of the three scores is 100%), or may output a classification result in a case where the endoscopic image can be clearly classified from the three scores. In the case of outputting a discrimination result, the output layer 562C may or may not include a fully connected layer as the last one or plural layers (see FIG. 4B).

The output layer 562C may output a measurement result of a region of interest. In the case of performing measurement by using the CNN, for example, the region of interest as a target may be segmented in the above-described manner and then measurement can be performed by the image processing unit 204 or the like on the basis of the result thereof. Alternatively, a measurement value of the region of interest as a target can be output directly from the recognizing unit 222. In the case where the measurement value is directly output, the image is caused to learn the measurement value, and thus regression of the measurement value occurs.

In the case of using the CNN having the above-described configuration, it is preferable to perform, in a learning procedure, a process of comparing a result output from the output layer 562C with a correct answer of recognition for the image set to calculate loss (error), and updating the weight parameters in the intermediate layer 562B from the layer on the output side toward the layer on the input side so that the loss is reduced (backpropagation).

Recognition Using Method Other than CNN

The recognizing unit 222 may perform recognition (detection or the like of a region of interest) by using a method other than the CNN. For example, a region of interest can be detected on the basis of a feature quantity of pixels of an acquired medical image. In this case, the recognizing unit 222 divides a detection target image into, for example, a plurality of rectangular regions, sets the rectangular regions obtained through the division as local regions, calculates, for each local region in the detection target image, a feature quantity (for example, hue) of pixels in the local region, and determines a local region having a specific hue among the local regions as a region of interest. Similarly, the recognizing unit 222 may perform classification or measurement based on a feature quantity.

Information Recorded in Recording Unit

Figure 6:
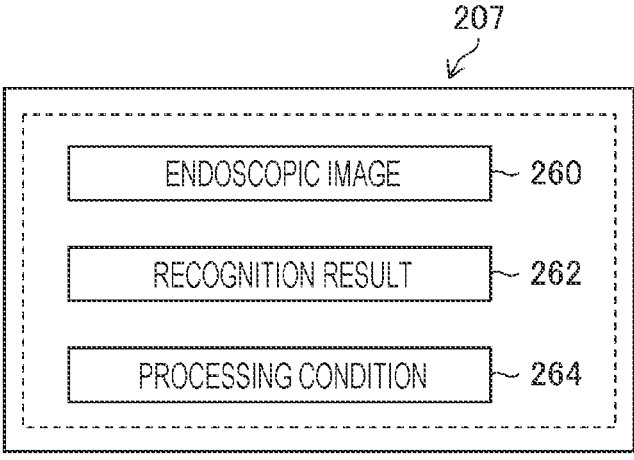
FIG. 6 is a diagram illustrating information recorded in a recording unit.

FIG. 6 is a diagram illustrating an example of information recorded in the recording unit 207. In the example in FIG. 6, an endoscopic image 260 (a medical image), a recognition result 262 (a result of recognition: detection, classification, measurement, etc.), and a processing condition 264 (ON/OFF, a style, and the like of reporting: see, for example, FIGS. 8 to 13) are recorded in association with each other under control by the recording control unit 230. The recording control unit 230 may record other information together.

Image Diagnosis Assistance Method

Figure 7:
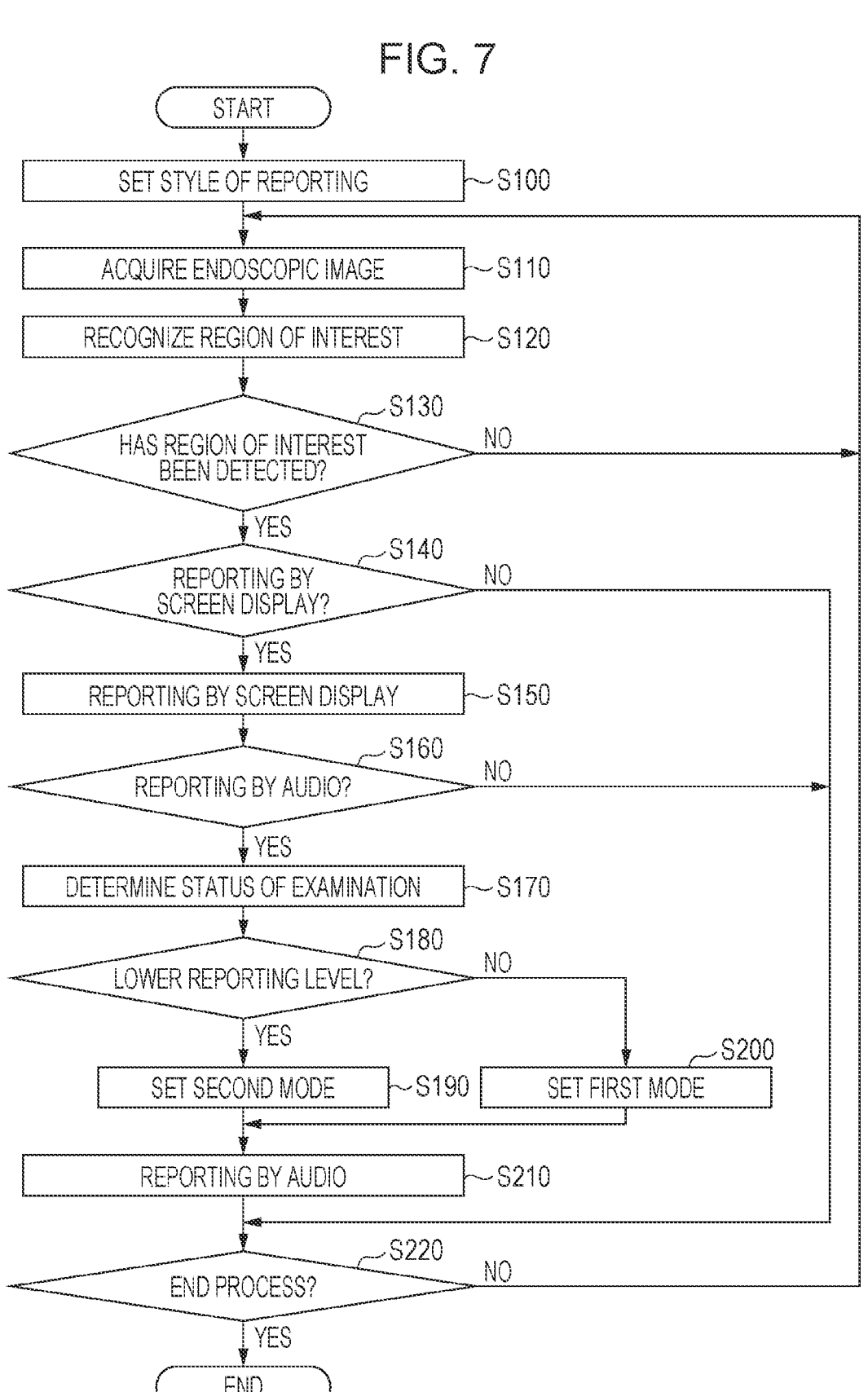
FIG. 7 is a flowchart illustrating a procedure of an image diagnosis assistance method according to the first embodiment.

An image diagnosis assistance method for the endoscope system 10 having the above-described configuration will be described with reference to the flowchart in FIG. 7. In the present embodiment, a description will be given mainly of a case where "recognition of a region of interest" is "detection of a region of interest". However, similar processing can be performed also in the case of "discrimination (classification) of a region of interest" or "measurement of a region of interest".

Setting of Reporting Style

The setting unit 228 sets a style of reporting (step S100: setting step). The setting unit 228 is capable of making this setting in accordance with a user operation performed via the operation unit 208 and the monitor 400, as will be described below, for example.

Reporting by Screen Display

FIG. 8 is a diagram illustrating an example of a setting screen for a style of reporting by screen display, and illustrates a state in which the setting unit 228 has displayed a screen 500 on the monitor 400 (broken lines in the figure are virtual lines indicating regions in the screen; the same applies to the following figures). The screen 500 has regions 502 to 508 in each of which radio buttons are disposed, and regions 510 to 514 in each of which a numerical value input field is disposed. A user is capable of setting whether reporting by screen display is to be performed (ON or OFF; region 502) by operating a radio button. Also, the user is capable of setting "whether reporting by display of a frame in an image region (for example, a frame 604 in FIG. 14A, 15A, or 15B) is to be performed" (region 504), "whether reporting by display of a frame outside an image region (for example, a frame 606 in FIG. 14B) is to be performed" (region 506), and "whether reporting by a symbol or figure (for example, a symbol 608 in FIG. 14C) is to be performed" (region 508) by operating a radio button. In addition, the setting unit 228 may set whether to display an image 601 (a frame 605 surrounding a region of interest 603 is illustrated) in which a lesion position is indicated in a region outside an observation image, as illustrated in FIG. 14D.

Furthermore, the user is capable of setting "an elapsed time from when a region of interest is detected to when reporting is started (to when switching from a non-reporting state to a reporting state occurs)" (region 510), "an elapsed time from the start to end of reporting (to when switching from the reporting state to the non-reporting state occurs)" (region 512), and "how many seconds before switching between a first mode and a second mode the notification of switching is performed" (region 514) by inputting a numerical value. In addition, the setting unit 228 may make a setting for performing screen display for a result obtained by temporally accumulating detection results in accordance with a user operation. For example, the setting unit 228 is capable of displaying a frame when a region of interest has been detected in consecutive five frames, and accordingly flicker of the screen resulting from a false detection can be prevented.

The reporting unit 224 is switched from the reporting state to the non-reporting state after a time (seconds) input to the region 512 has elapsed. For inputting a numerical value, a method of selecting a determined numerical value from a pull-down menu may be used. In the example in FIG. 8, reporting is "ON", display of a frame is "ON", the time from detection to start of reporting is 1.0 second, the time from the start to end of reporting is 1.5 seconds, and mode switching notification is performed at the same time as switching. With such switching to the non-reporting state, assistance can be finished and excessive assistance can be suppressed in accordance with needs of the user (in accordance with a predetermined condition).

The above-described example is an example of setting a style, and another item (reporting by light or vibration) may be set. In addition, the setting unit 228 may change settable items in accordance with the details of "recognition" (detection, discrimination, or measurement). For example, in the case of performing discrimination, the setting unit 228 is capable of setting ON/OFF of reporting and a reporting style regarding the type of a lesion, the range of a lesion, the size of a lesion, the macroscopic shape of a lesion, diagnosis of the stage of cancer, the present position in a lumen, the reliability of a discrimination result (computable with CNN), or the like. In addition, the reporting unit 224 may notify a user that the state of reporting will be switched between the reporting state and the non-reporting state, and the setting unit 228 may set a style of notification on the basis of a user operation performed via the operation unit 208 or the like.

Specific styles of reporting are illustrated in FIGS. 14A to 15B, which will be described below. A region for displaying a reporting style may be provided on the screen of the monitor 400 in accordance with a user operation (see a reporting style display region 610 in FIGS. 15A and 15B).

In this way, in the endoscope system 10 (an image diagnosis assistance apparatus, an endoscope system), a user is capable of setting a reporting style as appropriate and the reporting unit 224 performs assistance (reporting) in accordance with a set condition, and thus reporting can be appropriately performed by using screen display and audio while excessive reporting is suppressed. The setting of the style may be performed at any timing during processing, as well as at the start of medical image processing.

Reporting by Audio

FIG. 9 is a diagram illustrating an example of a setting screen for a style of reporting by audio, and illustrates a state in which the setting unit 228 has displayed a screen 520 on the monitor 400. The screen 520 has regions 522 to 528 in each of which radio buttons are disposed. A user is capable of setting whether reporting by audio is to be performed (ON or OFF; region 522), by operating a radio button. Also, the user is capable of setting "whether mode switching (the first mode and the second mode) based on a feature of a region of interest is to be performed" (region 524), "whether switching to the second mode based on duration of the first mode is to be performed" (region 526), and "whether mode switching (switching between the first mode and second mode) based on an examination status is to be performed" (region 528), by operating a radio button. The items in the regions 524 to 528 (specific criteria for mode switching) can be set in detail via the screens described below (see FIGS. 10 to 13). Switching between the first mode and the second mode is performed in accordance with a determination result of an examination status (described below).

Mode Switching Based on Feature of Region of Interest

Figures 10, 11:
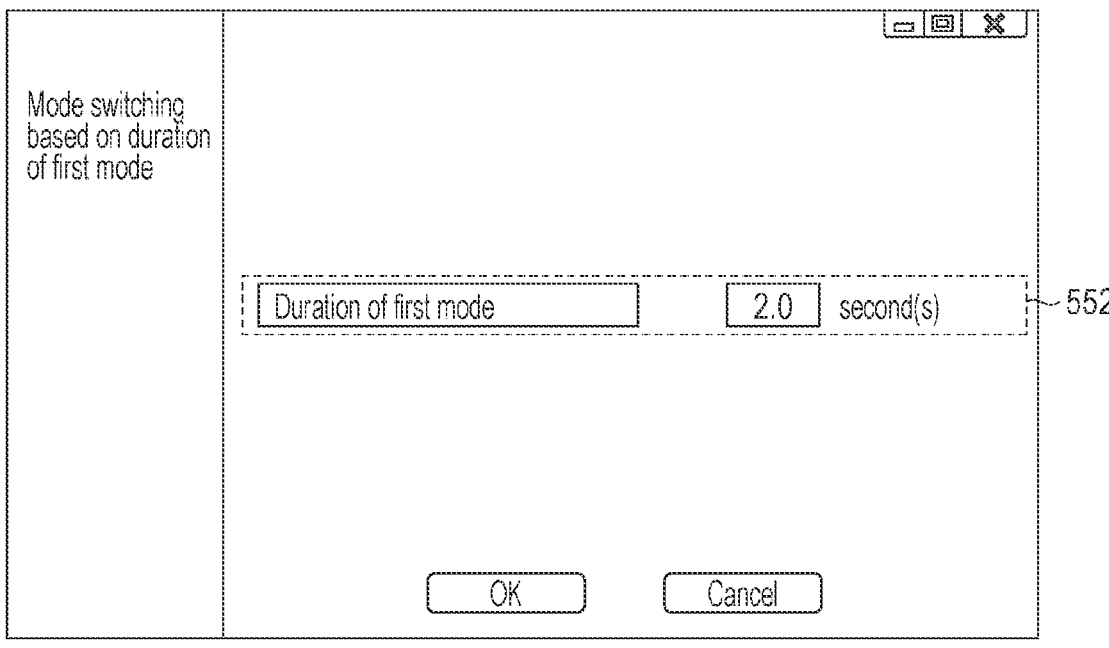
FIG. 10 is a diagram illustrating an example of a setting screen for mode switching based on a feature of a region of interest.
FIG. 11 is a diagram illustrating an example of a setting screen for mode switching based on duration of a first mode.

FIG. 10 is a diagram illustrating an example of a setting screen for mode switching based on a feature of a region of interest (details of setting in the region 524 in FIG. 9), and illustrates a state in which the setting unit 228 has displayed a screen 530 on the monitor 400. The screen 530 has regions 532 to 542 in each of which a radio button and a numerical value input field or a pull-down menu are disposed. A user is capable of setting criteria for switching based on the size, shape, position, and number of a region of interest (regions 532 to 538), and criteria for switching based on the lesion type of a region of interest (regions 540 and 542) by operating radio buttons and inputting a numerical value or performing selection. In the example in FIG. 10, in the region 532, if the size of a region of interest is 20 mm$^2$ or more (if the criterion is satisfied), the reporting unit 224 performs reporting in the second mode that uses audio having a second reporting level lower than a first reporting level (the second mode is continued). The size of a region of interest may be defined by the number of pixels. A situation in which a region of interest is large in an endoscopic image is that, for example, the user has been aware of the region of interest and has caused the tip end (imaging unit) of the endoscope 100 to approach the region of interest. As a result of performing reporting by audio in the second mode in such a case, reporting by audio can be appropriately performed with the reporting not disturbing observation.

The size of a region of interest in an image (the number of pixels of the region of interest) increases as the endoscope approaches the region of interest. When the region of interest is far and the size of the region of interest is smaller than a threshold value, reporting is performed in the first mode that uses audio having the first reporting level. When the size of the region of interest becomes larger than or equal to the threshold value as a result of approach to the region of interest, reporting is performed in the second mode having the second reporting level lower than the first reporting level. On the other hand, when a region of interest smaller than the threshold value is detected after approach to a region of interest and reporting in the second mode, reporting is performed in the first mode. This is a case in which a doctor (user) has overlooked a region of interest or a new region of interest has been detected, and it is necessary to cause the user to be aware of the region of interest. When the distance to a region of interest does not change and the size of the region of interest does not change, reporting may be continued in the first mode.

Switching Based on Duration of First Mode

FIG. 11 is a diagram illustrating an example of a setting screen for mode switching based on duration of the first mode (details of setting in the region 526 in FIG. 9), and illustrates a state in which the setting unit 228 has displayed a screen 550 on the monitor 400. The screen 550 has a region 552 in which a numerical value input field is disposed. A user is capable of setting duration of the first mode (the time during which reporting in the first mode is continuously performed on the same region of interest; determined by the determining unit 226) by inputting a numerical value. When reporting in the first mode is performed for the set time or more (a threshold value or more), the reporting unit 224 is switched to the second mode and performs reporting by audio. The mode is switched based on duration in this manner because, if reporting in the first mode continues for the set time or more, it is considered that the user has already been aware of a region of interest, and continuing reporting in a high reporting level (first mode) in such a situation may be disturbing.

Switching Based on Examination Status

Figures 12, 13:
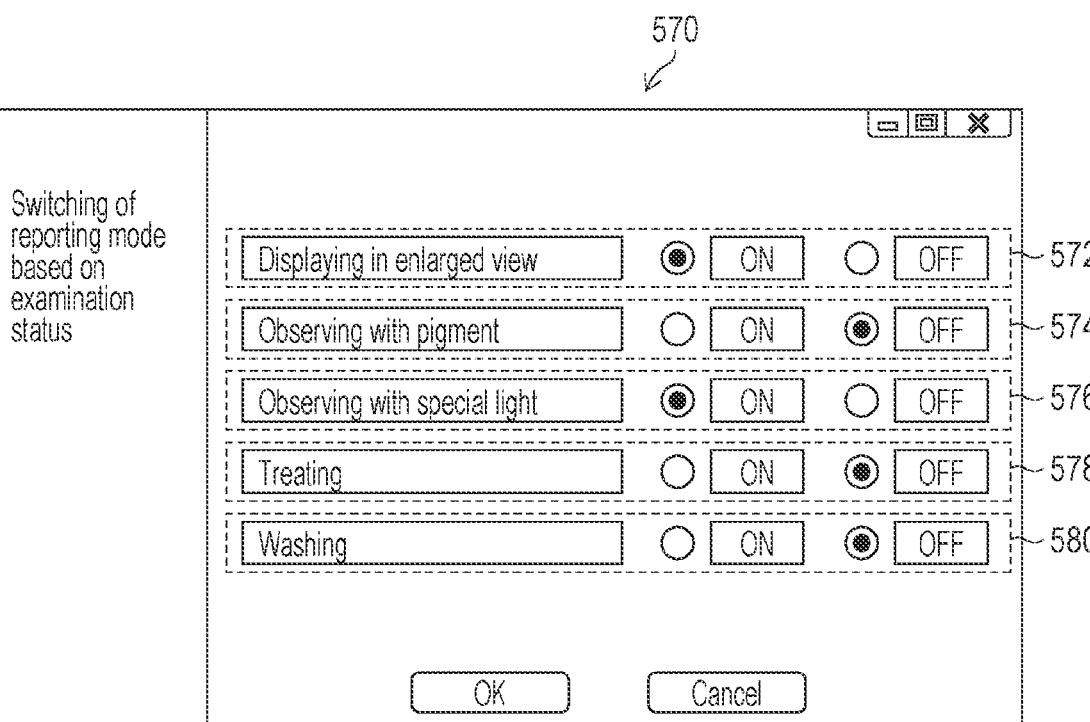
FIG. 12 is a diagram illustrating an example of a setting screen for mode switching based on an examination status.
FIG. 13 is a diagram illustrating an example of a setting screen for lowering a reporting level.

FIG. 12 is a diagram illustrating an example of a setting screen for mode switching based on an examination status (details of setting in the region 528 in FIG. 9), and illustrates a state in which the setting unit 228 has displayed a screen 570 on the monitor 400. The screen 570 has regions 572 to 580 in each of which a radio button is disposed. A user is capable of turning ON/OFF the mode switching based on an examination status by operating a radio button. Specifically, when the radio buttons in the regions 572 to 580 are ON, the reporting unit 224 performs reporting in the second mode when a medical image is being displayed in an enlarged view, when observation with pigment is being performed, when observation with special light is being performed, when treatment is being performed, and when washing is being performed. In these cases, it is considered that the user has been aware of a region of interest or that necessity of reporting is low. The user is capable of turn ON any one or more of the radio buttons in the regions 572 to 580 (when the user wants to turn OFF all, that is, when mode switching based on an examination status is not to be performed, the user may set the radio button to OFF in the region 528 in FIG. 9).

How to Lower Reporting Level

FIG. 13 is a diagram illustrating an example of a setting screen for lowering the reporting level in the second mode (comparison with the reporting level of the first mode), and illustrates a state in which the setting unit 228 has displayed a screen 590 on the monitor 400. The screen 590 has regions 592 to 596 in each of which radio buttons are disposed. A user is capable of setting one or more of lowering of volume, lowering of a tone, lowering of pitch, and stopping of reporting by audio, by operating a radio button.

Acquisition of Endoscopic Image

The image acquiring unit 220 acquires a chronological endoscopic image (medical image) (step S110: image acquisition step, execution of an image acquisition function). The image acquiring unit 220 may acquire an endoscopic image captured by the endoscope 100 or may acquire the endoscopic image 260 recorded in the recording unit 207. In a case where the image acquiring unit 220 acquires an endoscopic image captured by the endoscope 100, the recording control unit 230 is capable of recording the acquired image as the endoscopic image 260 in the recording unit 207.

Recognition of Region of Interest

The recognizing unit 222 (a recognizing unit: a detector, a classifier, a measurer) recognizes a region of interest in the endoscopic image acquired in step S110 (step S120: recognition step, execution of a recognition function). The recognizing unit 222 is capable of performing, as "recognition", one or more of detection, classification, and measurement by using the above-described CNN or the like. For example, in a case where the "recognition" is "detection" of a region of interest, examples of the region of interest (region of concern) to be detected may include a polyp, a cancer, a colon diverticulum, an inflammation, a treatment scar (a scar of endoscopic mucosal resection (EMR), a scar of endoscopic submucosal dissection (ESD), a clip portion, or the like), a bleeding point, a perforation, angiodysplasia, and the like. Examples of "discrimination" of a region of interest may be determination of the type of a lesion (hyperplastic polyp, adenoma, intramucosal cancer, invasive cancer, or the like), the range of a lesion, the size of a lesion, the macroscopic shape of a lesion, diagnosis of the stage of cancer, a current position in a lumen (a pharynx, an esophagus, a stomach, a duodenum, or the like in an upper portion; a cecum, an ascending colon, a transverse colon, a descending colon, a sigmoid colon, a rectum, or the like in a lower portion), and the like.

A description will be given below of a case where a region of interest has not been detected and the reporting unit 224 is in the non-reporting state in an initial state (at the start of processing).

Reporting by Screen Display

If the recognizing unit 222 has detected a region of interest (YES in step S130: recognition step, execution of a recognition function), the reporting unit 224 determines whether to perform reporting by screen display (step S140: reporting step, execution of a reporting function). Reporting by screen display is performed, for example, when the setting is ON (see the region 502 in FIG. 8) and the time "from detection of a region of interest to start of reporting" (see the region 510 in FIG. 8) has elapsed. Reporting by screen display is not performed, for example, when the setting is OFF or when the time "from detection of a region of interest to start of reporting" (see the region 510 in FIG. 8) has not elapsed although the setting is ON. In the case of performing reporting by screen display (YES in step S140), the reporting unit 224 is switched from the non-reporting state to the reporting state, and reports a recognition result in the style set in step S100 (for example, the frame 604 in FIG. 14A or the frame 606 in FIG. 14B) (step S150: reporting step, execution of a reporting function). The reporting unit 224 performs reporting by screen display regardless of a determination result of an examination status, but may change the style of screen display without giving a large influence to the reporting level. In the case of not performing reporting although a region of interest has been detected, the reporting unit 224 may be switched from the reporting state to the non-reporting state.

Reporting by Audio

The reporting unit 224 determines whether to perform reporting by audio (step S160: reporting step, execution of a reporting function). Reporting by audio is performed when the setting is ON (see the region 502 in FIG. 8).

Determination of Examination Status

In the case of performing reporting by audio (YES in step S160), the determining unit 226 determines an examination status (step S170: determination step, execution of a determination function). The determining unit 226 is capable of determining an examination status in accordance with an operation of the handheld operation section 102 (the air/water supply button 141 or the like) or the operation unit 208, acquisition of information on the light source control unit 350 (the type of observation light), or image processing on a medical image (whether enlarged display is being performed, detection of a treatment tool, determination of tint, or the like). In addition, the determining unit 226 may determine "whether a certain period has elapsed from the timing at which audio reporting is performed". For example, when 5 seconds have not elapsed from audio reporting, it is considered that the user's attention is attracted, and thus the reporting level of audio may be lowered.

Setting of Audio Reporting Mode, and Reporting by Audio

The reporting unit 224 determines, in accordance with the determination result in step S170, whether to lower the reporting level of reporting by audio, that is, which of the first mode and the second mode is to be used to perform reporting (step S180: reporting step, execution of a reporting function). The reporting unit 224 is capable of making a determination in step S180 in accordance with the "criteria for mode switching" (see the regions 524 to 528 in FIG. 9; a feature of a region of interest in the example in the figure) set in step S100. The reporting unit 224 sets either of the first mode and the second mode in accordance with the determination result in step S180 (step S190 or S200: reporting step, execution of a reporting function), and performs reporting by audio in the set mode (step S210: reporting step, execution of a reporting function). The reporting unit 224 may perform reporting by audio by switching the mode from the first mode to the second mode, or from the second mode to the first mode, in accordance with the determination result of the examination status. The reporting unit 224 may continue reporting in the first mode or the second mode in accordance with the determination result of the examination status. An audio type may be electronic sound or human voice. In the case of electronic sound, sound that can be distinguished from environmental sound in an examination room (the sound of a heartrate meter or an exhaust sound) is preferred.

Examples of Reporting by Screen Display

Figure 14A:
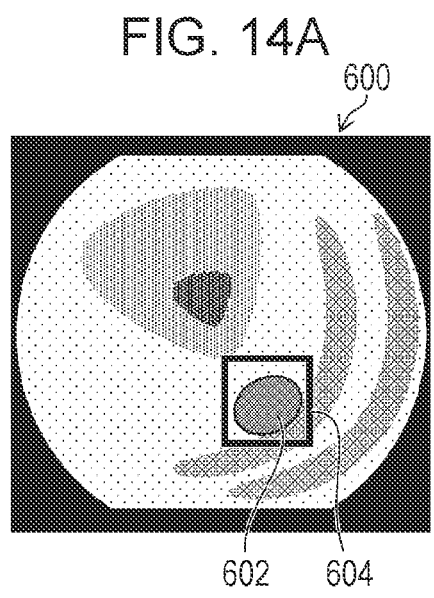
FIGS. 14A to 14D are diagrams illustrating states of reporting by screen display.
Figure 14B:
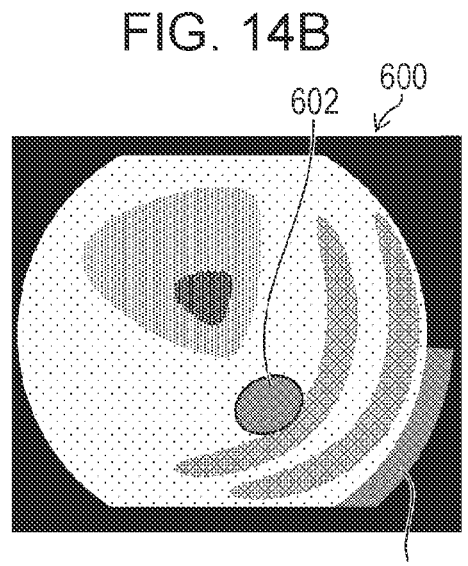
Figure 14C:
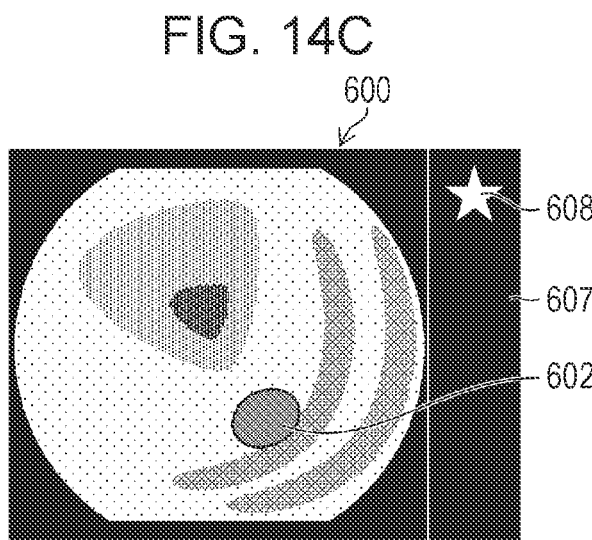
Figure 14D:
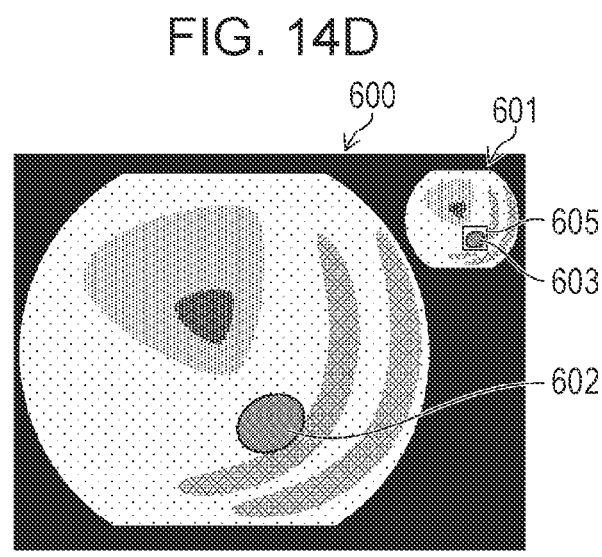

FIGS. 14A to 14D are diagrams illustrating examples of reporting by screen display (step S150). FIG. 14A illustrates a state in which a region of interest 602 is seen in an image display region 600 on the monitor 400, and the frame 604 surrounding the region of interest 602 is further displayed (a case where the radio button is ON in the region 504 in FIG. 8). Similarly, FIG. 14B illustrates a state in which the frame 606 is displayed outside the image display region 600 (a case where the radio button is ON in the region 506 in FIG. 8), and FIG. 14C illustrates a state in which the star-shaped symbol 608 is displayed in a reporting region 607 provided outside the image display region 600.

States of Reporting by Audio

Figure 15A:
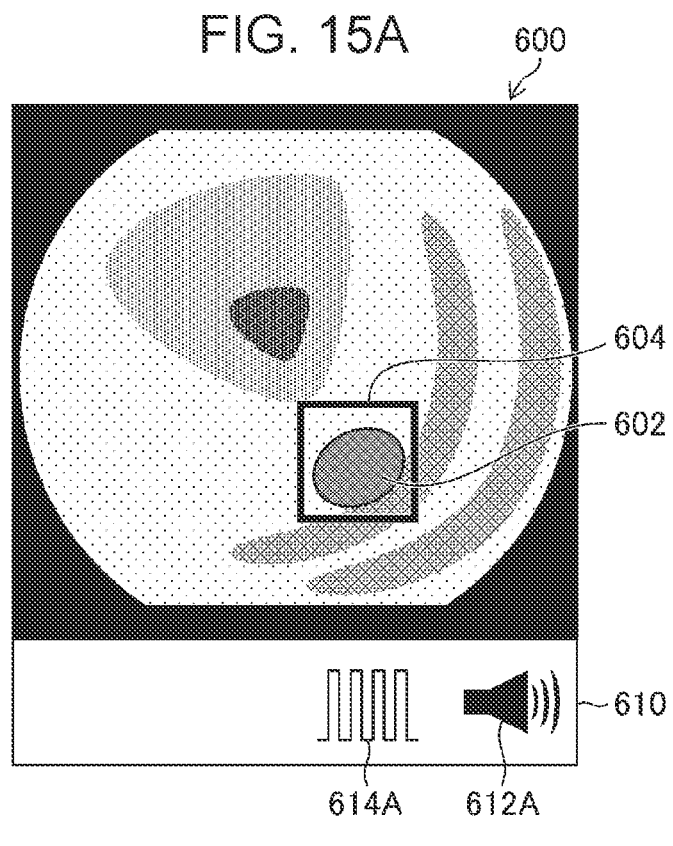
FIGS. 15A and 15B are diagrams illustrating examples of a state in which reporting by audio is set.
Figure 15B:
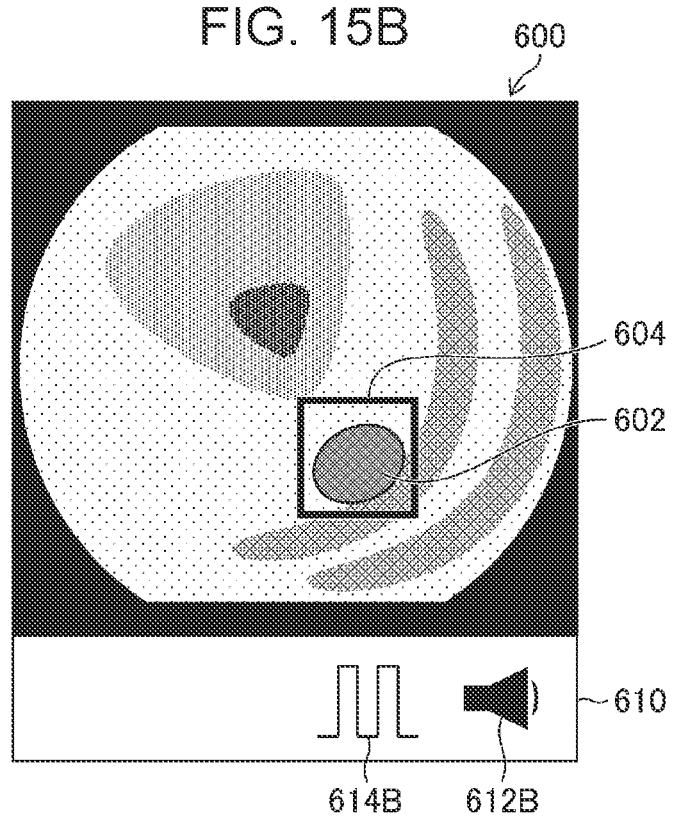

FIGS. 15A and 15B are diagrams illustrating states of reporting by audio (step S210). FIG. 15A illustrates an example of a state of reporting in the first mode, in which the reporting style display region 610 is provided outside the image display region 600, and an icon 612A indicating the volume of audio output (high volume) and an icon 614A indicating the pitch of audio (high pitch and short period) are displayed. In contrast, FIG. 15B illustrates an example of a state of reporting in the second mode, in which an icon 612B indicating the volume of audio output (low volume) and an icon 614B indicating the pitch of audio (low pitch of ON/OFF and long period) are displayed. The state illustrated in FIG. 15B (a reporting state in the second mode) corresponds to the settings of a reporting style in FIG. 13. The reporting unit 224 may erase these icons and the reporting style display region 610 after a determined time from start of reporting or in accordance with a user operation performed via the operation unit 208 or the like.

End of Process

The image processing unit 204 repeats the process of step S110 to step S210 until the process ends (until "YES" is obtained in step S220). The image processing unit 204 is capable of ending the process in accordance with, for example, a user operation performed on the handheld operation section 102 or the operation unit 208.

Advantages of Embodiment

As described above, the endoscope system 10 according to the present embodiment is capable of using audio having an appropriate reporting level in accordance with an examination status and capable of appropriately performing reporting by using screen display and audio. In addition, a user is capable of easily grasping a state of reporting by audio in accordance with an icon displayed in the reporting style display region 610.

Recognition of Region of Interest Using Method Other than Image Processing

In the embodiment described above, a description has been given of the case of recognizing a region of interest by using image processing on a medical image, but the recognizing unit 222 may recognize a region of interest without using image processing on a medical image (step S120: recognition step). The recognizing unit 222 is capable of recognizing (detecting, discriminating (classifying), measuring) a region of interest by using, for example, audio input, image recognition of a gesture, or an operation of a device such as a foot switch, of a user. In addition, in the image diagnosis assistance apparatus, the endoscope system, and the image diagnosis assistance method according to the present invention, reporting and notification are performed similarly to the above-described embodiment also in the case of performing recognition without using processing on a medical image, and this makes it possible to appropriately perform reporting by using screen display and audio.

Application to Images Other than Endoscopic Image

In the above-described embodiment, a description has been given of the case of performing recognition by using an endoscopic image, which is an aspect of a medical image. The image diagnosis assistance apparatus and the image diagnosis assistance method according to the present invention can also be applied to the case of using a medical image other than an endoscopic image, such as an ultrasound image.

APPENDICES

In addition to the above-described embodiment, the configurations described below are included in the scope of the present invention.

Appendix 1

A medical image processing apparatus wherein
a medical image analysis processing unit detects a region of interest on the basis of a feature quantity of pixels of a medical image, the region of interest being a region to be focused on, and
a medical image analysis result acquiring unit acquires an analysis result of the medical image analysis processing unit.

Appendix 2

A medical image processing apparatus wherein
a medical image analysis processing unit detects presence or absence of a target to be focused on the basis of a feature quantity of pixels of a medical image, and
a medical image analysis result acquiring unit acquires an analysis result of the medical image analysis processing unit.

Appendix 3

The medical image processing apparatus wherein
the medical image analysis result acquiring unit acquires the analysis result of the medical image from a recording device in which the analysis result is recorded, and
the analysis result is either or both of the region of interest which is a region to be focused on included in the medical image and the presence or absence of the target to be focused on.

Appendix 4

The medical image processing apparatus wherein the medical image is a normal-light image acquired by radiating light in a white range or light in a plurality of wavelength ranges as the light in the white range.

Appendix 5

The medical image processing apparatus wherein
the medical image is an image acquired by radiating light in a specific wavelength range, and
the specific wavelength range is a range narrower than a white wavelength range.

Appendix 6

The medical image processing apparatus wherein the specific wavelength range is a blue or green range in a visible range.

Appendix 7

The medical image processing apparatus wherein the specific wavelength range includes a wavelength range of 390 nm or more and 450 nm or less or a wavelength range of 530 nm or more and 550 nm or less, and the light in the specific wavelength range has a peak wavelength in the wavelength range of 390 nm or more and 450 nm or less or the wavelength range of 530 nm or more and 550 nm or less.

Appendix 8

The medical image processing apparatus wherein the specific wavelength range is a red range in a visible range.

Appendix 9

The medical image processing apparatus wherein the specific wavelength range includes a wavelength range of 585 nm or more and 615 nm or less or a wavelength range of 610 nm or more and 730 nm or less, and the light in the specific wavelength range has a peak wavelength in the wavelength range of 585 nm or more and 615 nm or less or the wavelength range of 610 nm or more and 730 nm or less.

Appendix 10

The medical image processing apparatus wherein the specific wavelength range includes a wavelength range in which a light absorption coefficient is different between oxyhemoglobin and deoxyhemoglobin, and the light in the specific wavelength range has a peak wavelength in the wavelength range in which the light absorption coefficient is different between oxyhemoglobin and deoxyhemoglobin.

Appendix 11

The medical image processing apparatus wherein the specific wavelength range includes a wavelength range of 400±10 nm, a wavelength range of 440±10 nm, a wavelength range of 470±10 nm, or a wavelength range of 600 nm or more and 750 nm or less, and the light in the specific wavelength range has a peak wavelength in the wavelength range of 400±10 nm, the wavelength range of 440±10 nm, the wavelength range of 470±10 nm, or the wavelength range of 600 nm or more and 750 nm or less.

Appendix 12

The medical image processing apparatus wherein
the medical image is an inside-of-living-body image depicting an inside of a living body, and
the inside-of-living-body image has information about fluorescence emitted by a fluorescent substance in the living body.

Appendix 13

The medical image processing apparatus wherein the fluorescence is acquired by irradiating the inside of the living body with excitation light whose peak is 390 nm or more and 470 nm or less.

Appendix 14

The medical image processing apparatus wherein
the medical image is an inside-of-living-body image depicting an inside of a living body, and
the specific wavelength range is a wavelength range of infrared light.

Appendix 15

The medical image processing apparatus wherein the specific wavelength range includes a wavelength range of 790 nm or more and 820 nm or less or a wavelength range of 905 nm or more and 970 nm or less, and the light in the specific wavelength range has a peak wavelength in the wavelength range of 790 nm or more and 820 nm or less or the wavelength range of 905 nm or more and 970 nm or less.

Appendix 16

The medical image processing apparatus wherein
a medical image acquiring unit includes a special-light image acquiring unit that acquires a special-light image having information about the specific wavelength range on the basis of a normal-light image that is acquired by radiating light in a white range or light in a plurality of wavelength ranges as the light in the white range, and
the medical image is the special-light image.

Appendix 17

The medical image processing apparatus wherein a signal in the specific wavelength range is acquired through computation based on color information of RGB or CMY included in the normal-light image.

Appendix 18

The medical image processing apparatus including
a feature quantity image generating unit that generates a feature quantity image through computation based on at least one of a normal-light image or a special-light image, the normal-light image being acquired by radiating light in a white range or light in a plurality of wavelength ranges as the light in the white range, the special-light image being acquired by radiating light in a specific wavelength range, wherein
the medical image is the feature quantity image.

Appendix 19

An endoscope apparatus including:
the medical image processing apparatus according to any one of appendices 1 to 18; and
an endoscope that acquires an image by radiating at least any one of light in a white wavelength range or light in a specific wavelength range.

Appendix 20

A diagnosis assistance apparatus including the medical image processing apparatus according to any one of appendices 1 to 18.

Appendix 21

A medical work assistance apparatus including the medical image processing apparatus according to any one of appendices 1 to 18.

The embodiment of the present invention and other examples have been described above. The present invention is not limited to the above-described aspects and various modifications can be made without deviating from the spirit of the present invention.

REFERENCE SIGNS LIST 10 endoscope system
100 endoscope
102 handheld operation section
104 insertion section
106 universal cable
108 light guide connector
112 soft part
114 bending part
116 tip rigid part
116A distal-end-side surface
123 illumination unit
123A illumination lens
123B illumination lens
126 forceps port
130 imaging optical system
132 imaging lens
134 imaging element
136 driving circuit
138 AFE
141 air/water supply button
142 suction button
143 function button
144 imaging button
170 light guide
200 processor
202 image input controller
204 image processing unit
205 communication control unit
206 video output unit
207 recording unit
208 operation unit
209 audio processing unit
209A speaker
210 CPU
211 ROM
212 RAM
220 image acquiring unit
222 recognizing unit
224 reporting unit
226 determining unit
228 setting unit
230 recording control unit
260 endoscopic image
262 recognition result
264 processing condition
300 light source apparatus
310 light source
310B blue light source
310G green light source
310R red light source
310V violet light source
330 diaphragm
340 condenser lens
350 light source control unit
400 monitor
500 screen
502 region
504 region
506 region
508 region
510 region
512 region
514 region
520 screen
522 region 524 region
526 region
528 region
530 screen
532 region
534 region
536 region
538 region
540 region
542 region
550 screen
552 region
562 CNN
562A input layer
562B intermediate layer
562C output layer
564 convolutional layer
565 pooling layer
566 fully connected layer
570 screen
572 region
574 region
576 region
578 region
580 region
590 screen
592 region
593 region
594 region
596 region
600 image display region
601 image
602 region of interest
603 region of interest
604 frame
605 frame
606 frame
607 reporting region
608 symbol
610 reporting style display region
612A icon
612B icon
614A icon
614B icon
$F_1$ filter
$F_2$ filter
S100 to S220 individual steps of image diagnosis assistance method

What is claimed is:

1. An image diagnosis assistance apparatus comprising:
one or more processors configured to:
acquire a plurality of medical images sequentially captured by an endoscope including an insertion section that is inserted into a living body and a handheld operation section that is connected to the insertion section;
perform recognitions of a region of interest in the plurality of medical images;
perform reporting of results of the recognitions by using screen display and audio;
make a determination on an examination status; and
perform reporting by using the audio in a first mode of using a first audio having a first reporting level in a case where the plurality of medical images are captured by radiating a first illumination light from the endoscope and a second mode of using a second audio having a second reporting level lower than the first reporting level in a case where the plurality of medical images are captured by radiating a second illumination light from the endoscope, in accordance with a result of the determination, wherein a wavelength range of the second illumination light is narrower than a wavelength range of the first illumination light, and the one or more processors are further configured to:

determine a time during which reporting in the first mode is continuously being performed on the region of interest, and in a case where the time is longer than or equal to a threshold value, switch to the second mode and perform reporting, and perform reporting in the second mode by at least one of making volume of the second audio lower than volume of the first audio in the first mode, making a tone of the second audio lower than a tone of the first audio in the first mode, making pitch of the second audio lower than pitch of the first audio in the first mode, or stopping reporting by the audio.

2. The image diagnosis assistance apparatus according to claim 1, wherein the one or more processors are further configured to:

recognize a feature of the region of interest, determine whether the feature satisfies a criterion, and perform reporting in the second mode in a case where a determination is made that the feature satisfies the criterion.

3. The image diagnosis assistance apparatus according to claim 2, wherein the one or more processors are further configured to:

recognize, as the feature, at least one of a size, a position, a shape, a number, or a lesion type of the region of interest, and perform reporting in the second mode in a case where the recognized feature satisfies the criterion.

4. An endoscope system comprising:

the image diagnosis assistance apparatus according to claim 1;

a display apparatus that displays the plurality of medical images; and the endoscope, the endoscope including an imaging unit that captures the plurality of medical images.

5. An image diagnosis assistance method comprising:

an image acquisition step of acquiring a plurality of medical images sequentially captured by an endoscope including an insertion section that is inserted into a living body and a handheld operation section that is connected to the insertion section;

a recognition step of performing recognitions of a region of interest in the plurality of medical images;

a reporting step of performing reporting of results of the recognitions by using screen display and audio;

a determination step of making a determination on an examination status; and performing reporting by using the audio in a first mode of using a first audio having a first reporting level in a case where the plurality of medical images are captured by radiating a first illumination light from the endoscope and a second mode of using a second audio having a second reporting level lower than the first reporting level in a case where the plurality of medical images are captured by radiating a second illumination light from the endoscope, in accordance with a result of the determination, wherein a wavelength range of the second illumination light is narrower than a wavelength range of the first illumination light, and the image diagnosis assistance method further comprises:

determining a time during which reporting in the first mode is continuously being performed on the region of interest, in a case where the time is longer than or equal to a threshold value, switching to the second mode and perform reporting, and performing reporting in the second mode by at least one of making volume of the second audio lower than volume of the first audio in the first mode, making a tone of the second audio lower than a tone of the first audio in the first mode, making pitch of the second audio lower than pitch of the first audio in the first mode, or stopping reporting by the audio.

6. A non-transitory computer-readable recording medium, wherein the non-transitory computer-readable recording medium stores instructions which, when read by a computer, cause the computer to execute the image diagnosis assistance method according to claim 5.

7. An image diagnosis assistance apparatus comprising:

one or more processors configured to:

acquire a plurality of medical images sequentially captured by an endoscope including an insertion section that is inserted into a living body and a handheld operation section that is connected to the insertion section;

perform recognitions of a region of interest in the plurality of medical images;

perform reporting of results of the recognitions by using screen display and audio;

make a determination on an examination status; and perform reporting by using the audio in a first mode of using a first audio having a first reporting level in a case where the plurality of medical images are captured by radiating a first illumination light from the endoscope and a second mode of using a second audio having a second reporting level lower than the first reporting level in a case where the plurality of medical images are captured by radiating a second illumination light from the endoscope, in accordance with a result of the determination, wherein a wavelength range of the second illumination light is narrower than a wavelength range of the first illumination light, and the one or more processors are further configured to:

perform reporting in the second mode in a case where a result of the determination indicates any one or more of that the plurality of medical images is being displayed in an enlarged view, that observation with pigment is being performed, that observation with special light is being performed, that treatment is being performed, and that washing is being performed, and perform reporting in the second mode by at least one of making volume of the second audio lower than volume of the first audio in the first mode, making a tone of the second audio lower than a tone of the first audio in the first mode, making pitch of the second audio lower than pitch of the first audio in the first mode, or stopping reporting by the audio.

8. The image diagnosis assistance apparatus according to claim 7, wherein the one or more processors are further configured to:

recognize a feature of the region of interest, determine whether the feature satisfies a criterion, and perform reporting in the second mode in a case where a determination is made that the feature satisfies the criterion.

9. The image diagnosis assistance apparatus according to claim 8, wherein the one or more processors are further configured to:

recognize, as the feature, at least one of a size, a position, a shape, a number, or a lesion type of the region of interest, and perform reporting in the second mode in a case where the recognized feature satisfies the criterion.

10. An endoscope system comprising:

the image diagnosis assistance apparatus according to claim 7;

a display apparatus that displays the plurality of medical images; and the endoscope, the endoscope including an imaging unit that captures the plurality of medical images.

11. An image diagnosis assistance method comprising:

an image acquisition step of acquiring a plurality of medical images sequentially captured by an endoscope including an insertion section that is inserted into a living body and a handheld operation section that is connected to the insertion section;

a recognition step of performing recognitions of a region of interest in the plurality of medical images;

a reporting step of performing reporting of results of the recognitions by using screen display and audio;

a determination step of making a determination on an examination status; and performing reporting by using the audio in a first mode of using a first audio having a first reporting level in a case where the plurality of medical images are captured by radiating a first illumination light from the endoscope and a second mode of using a second audio having a second reporting level lower than the first reporting level in a case where the plurality of medical images are captured by radiating a second illumination light from the endoscope, in accordance with a result of the determination, wherein a wavelength range of the second illumination light is narrower than a wavelength range of the first illumination light, and the image diagnosis assistance method further comprises performing reporting in the second mode in a case where a result of the determination indicates any one or more of that the plurality of medical images is being displayed in an enlarged view, that observation with pigment is being performed, that observation with special light is being performed, that treatment is being performed, and that washing is being performed, and performing reporting in the second mode by at least one of making volume of the second audio lower than volume of the first audio in the first mode, making a tone of the second audio lower than a tone of the first audio in the first mode, making pitch of the second audio lower than pitch of the first audio in the first mode, or stopping reporting by the audio.

12. A non-transitory computer-readable recording medium, wherein the non-transitory computer-readable recording medium stores instructions which, when read by a computer, cause the computer to execute the image diagnosis assistance method according to claim 11.

* * * * *